United States Patent [19]
Chuck et al.

[11] Patent Number: 5,534,660
[45] Date of Patent: Jul. 9, 1996

[54] Ph GENES AND THEIR USES

[75] Inventors: George S. Chuck, Berkeley; Hugo K. Dooner, Walnut Creek; Neal Courtney-Gutterson, Oakland; Janis Keller, Castro Valley; Charanjit S. Nijjar, Richmond; Edward J. Ralston, Pleasant Hill, all of Calif.

[73] Assignee: DNA Plant Technology Corporation, Oakland, Calif.

[21] Appl. No.: 49,282

[22] Filed: Apr. 16, 1993

[51] Int. Cl.$^6$ .............................. A01H 1/04; A01H 5/02; C12N 15/10; C12N 15/63; C07H 19/00

[52] U.S. Cl. ................ 800/205; 800/200; 800/250; 800/255; 800/DIG. 67; 435/172.3; 435/320.1; 435/6; 536/22.1; 536/23.1; 536/23.6; 536/24.1; 536/24.5

[58] Field of Search ........................ 800/200, 205, 800/230, 255, 250, DIG. 44, DIG. 67; PLT/1–29; 435/6, 172.3, 240.1, 240.4, 240.49, 320.1; 935/11, 35, 55, 67; 536/22.1, 23.1, 23.6, 24.1, 24.5

[56] References Cited

U.S. PATENT DOCUMENTS

| | | | |
|---|---|---|---|
| 5,073,676 | 12/1991 | Bridges et al. | 800/205 |
| 5,283,184 | 2/1994 | Jorgensen | 435/172.3 |
| 5,286,635 | 2/1994 | Hanson et al. | 435/172.3 |

OTHER PUBLICATIONS

Gerats et al. 1989 Developmental Genetics 10:561–568.
Haring et al. 1991 Plant Molecular Biology, 16:449–461.
de Vlaming et al. 1983 Theor. Appl. Genet. 66:271–278.
Gerats et al. 1990 The Plant Cell 2:1121–1128.
Napoli et al. 1990 The Plant Cell 2:279–289.
Wiering et al. 1984 In Monographs on Theoretical and Applied Genetics vol. 9 Frankel et al., eds. pp. 49–67.
Boswell et al. 1988 In Computational Molecular Biology Sources and Methods for Sequence Analysis Lesk, ed. pp. 169–171.
Ludwig, Steven R., et al., (1989) "Lc, a member of the maize R gene family responsible for tissue-specific anthocaynin production, encodes a protein similar to transcriptional activators and contains the myc–homology region", *Proc. Natl. Acad. Sci. USA*, 86:7092–7096.
de Vlaming, P. et al. (1982) "A Gene for Flower Colour Fading in *Petunia hybrida*", *Theor. Appl. Genet.* 61:41–46.

Primary Examiner—David T. Fox
Assistant Examiner—Erich E. Veitenheimer
Attorney, Agent, or Firm—Townsend and Townsend and Crew

[57] ABSTRACT

The present invention provides compositions and methods for regulating vacuolar pH. Isolated DNA constructs comprising sequences substantially identical to a Ph gene are provided. The methods typically involve introducing the construct into a plant, whereby vacuolar pH is modified in the transgenic plant.

27 Claims, 6 Drawing Sheets

PH GENES AND THEIR USES

BACKGROUND OF THE INVENTION

The present invention relates to compositions and methods for controlling intra-cellular pH, e.g., vacuolar pH in plant cells. In particular, it relates to the isolation and characterization of Ph genes and their use in controlling vacuolar pH.

The vacuole is an important component of plant cells and often accounts for the majority of the cell volume. The vacuole contains water and a variety of organic and inorganic compounds such as sugars, organic acids, proteins, anthocyanin pigments and excretory products such as calcium oxalate and tannin compounds.

The vacuole is surrounded by a membrane (tonoplast membrane) which regulates the movement of materials into and out of the vacuole. Thus, the plant cell controls the contents of the fluid or cell sap within the vacuole. One of the properties of the cell sap which is regulated by the plant cell is proton concentration or pH of the solution.

A number of proteins can affect vacuolar pH. For instance, vacuolar ATPases generate pH and electrical gradients by hydrolyzing ATP and pumping protons across the tonoplast membrane. Nelson et al., *Trends in Biochemical Science,* 14:113–116 (1989). Another enzyme that affects vacuolar pH is inorganic pyrophosphatase. In Arabidopsis, this enzyme is a single 81 kDa protein that is encoded by a single gene (Sarafian et al., *Proc. Natl. Acad. Sci. USA* 89:1775–1779 (1992).

A group of genes in plants, referred to as Ph genes, encode proteins that also affect vacuolar pH. In *Petunia hybrida* (petunia) a number of Ph genes are known to play a role in determining vacuolar pH, although none has been reported as isolated or sequenced. de Vlaming et al. *Theor. Appl. Genet.* 66:271–278 (1983) and Wiering, et al., in *Monographs on Theoretical and Applied Genetics* 9: Petunia, K. C. Sink, ed. (Springer-Verlag, Berlin 1984), pp. 49–67, Gerats et al., *Dev. Gen.* 10:561–568 (1989) all of which are incorporated herein by reference.

In yeast, at least 17 different vph (vacuolar pH genes) required for acidification have been identified. For example, the vph1 mutation causes an elevation of vacuolar pH. Preston et al., *Proc. Natl. Acad. Sci. USA* 86:7027–7031 (1989). This mutant has been shown to lack ATPase activity as a consequence of a lesion in a gene encoding a 95 kDa integral membrane subunit of the ATPase. Manolson et al. *J. Biol. Chem.* 267:14294–14303 (1992). A second vph mutant, vat2, is defective in the synthesis of the 60 kDa subunit of ATPase and also exhibits an elevated vacuolar pH. Nelson et al. *Proc. Natl. Acad. Sci. USA* 87:3503–3507 (1990).

Vacuolar pH is important in determining a number of plant traits. For instance, in petunia, certain forms of anthocyanins have been shown to appear red at low pH (e.g., pH 5.5) and blue at higher pH values (e.g., pH 5.9). Timberlake et al., in *The Flavonoids,* Harborne, et al. eds. (Academic Press, New York, 1975) pp.214–266. Thus, flower color has been shown to change as the pH of the corolla cell vacuole is altered. In addition, the acidity of fruits such as tomatoes or citrus fruits depends upon the pH of the vacuolar contents. Other traits known to be affected by vacuolar pH include seed coat development, female fertility, protein transport.

There is currently a need for methods of producing new plant varieties with modified traits affected by vacuolar pH, such as flower color and fruit acidity. Control of the expression of genes encoding proteins affecting vacuolar pH provides a useful approach to this problem. The present invention addresses these and other needs.

SUMMARY OF THE INVENTION

The present invention provides isolated DNA constructs comprising a polynucleotide sequence from a Ph gene. As defined here, Ph genes encode proteins which regulate vacuolar pH. Preferably, the Ph gene regulates pH by controlling transcription of one or more genes (i.e., downstream genes) which in turn encode proteins which directly regulate vacuolar pH. The protein encoded by such Ph genes typically comprises a transcriptional activator sequence in particular, a helix-loop-helix motif. This motif is characteristic of the myc family of eukaryotic transcriptional activators. A preferred embodiment of the pH gene comprises sequences substantially identical to sequences which are, or which are contained within, SEQ. ID. No. 1.

Also within the invention are genes the mutation of which confer one or more of the following characteristics on a plant compared to wild type: 1) increased vacuolar pH; 2) flower color shift from red toward blue as a result of pH effect on anthocyanin pigments; 3) enhanced fading of flower color with aging; and 4) appearance of seeds as shrivelled or irregular and having less pigment.

The constructs of the invention are used to alter the vacuolar pH of plant organs or parts such as flowers or fruit, typically by modifying expression of an endogenous Ph gene. Thus, the DNA construct may further comprise a promoter operably linked to the polynucleotide sequence. The promoter is preferably a plant promoter such as a fruit-specific promoter or a flower-specific promoter. If suppression of the endogenous Ph gene is desired, the polynucleotide sequence may be linked to the promoter in the sense or antisense orientations.

The invention also provides transgenic plants (e.g., petunia plants or tomato plants) comprising a recombinant expression cassette which includes a plant promoter operably linked to the polynucleotide sequence. The transgenic plants exhibit altered vacuolar pH in one or more types of tissues. For many purposes, the introduction of the recombinant expression cassettes preferably results in inhibition of an endogenous Ph gene, resulting in plants with increased vacuolar pH.

The invention further provides a method of altering vacuolar pH in a plant. The method comprises introducing into plant tissue a recombinant expression cassette comprising a plant promoter operably linked to a polynucleotide sequence from a Ph gene, in the sense or the antisense orientation. The promoter may be a tissue-specific promoter, e.g., a fruit-specific promoter or a flower-specific promoter. The expression cassette is typically introduced into the plant tissue using Agrobacterium or other standard means. The transformed plant tissue is regenerated into whole plants, whereby normally the regenerated plant transcribes the introduced polynucleotide sequence. The plants are then assayed and selected for altered vacuolar pH.

The invention further provides methods of isolating a Ph gene from a plant. The method may comprise probing a DNA library (e.g., a cDNA library) prepared from the plant with oligonucleotide probes comprising a polynucleotide sequence from an isolated Ph gene. Alternatively, the method may comprise transforming plants with a DNA construct comprising a transposon (e.g., the Ac transposon) and assaying the plants for increased vacuolar pH resulting from the transposon excising from the DNA construct and inserting in a Ph gene. Those plants having increased vacuolar pH are then selected. A preferred method uses a transposon inserted in a streptomycin resistance gene such that the gene is inoperable. Plants in which the transposon has excised from the gene are identified by the ability to grow on streptomycin.

Definitions

The phrase "nucleic acid sequence" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

The term "promoter" refers to a region of DNA upstream from the start of transcription and involved in recognition and binding of RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

A "heterologous sequence" is one that originates from a foreign species, or, if from the same species, is substantially modified from its original form. For example, a heterologous promoter operably lifted to structural gene is from a species different from that from which the structural gene was derived, or, if from the same species, is substantially modified from its original form.

A "polynucleotide sequence from a Ph gene" is a subsequence or full length polynucleotide sequence of a Ph gene, such as the Ph6 gene, which, when present in a transgenic plant has the desired effect, for example, inhibiting expression of the endogenous Ph gene. In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term "polynucleotide sequence from a Ph gene" specifically includes those full length sequences substantially identical (determined as described below) with a Ph gene sequence and that encode proteins that retain the function of the Ph protein. Thus, in the case of Ph6 gene disclosed here, the above term includes variant polynucleotide sequences which have substantial identity with the sequences disclosed here and which encode proteins capable of altering vacuolar pH as detected in the assays described below.

In the case of polynucleotides used to inhibit expression of an endogenous gene, the introduced sequence also need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection. These references are incorporated herein by reference.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BESTFIT) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%.

In the case of Ph genes and proteins of the invention, sequences are preferably compared in regions outside the conserved helix-loop-helix region characteristic of transcriptional activators as described below. Unrelated transcriptional activators may have high sequence identity only in the helix-loop-helix region, whereas Ph genes of the invention are substantially identical to the sequences disclosed here in the helix-loop-helix region as well as sequences outside this region.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C.

As used herein a "Ph gene" is a gene encoding a protein, other than an ATPase or pyrophosphatase, that regulates or affects vacuolar pH. Ph genes typically affect a number of plant characteristics including flower color, stability of flower color over time, fertility and seed appearance.

A Ph gene may be identified and defined based upon the fact that when normal Ph gene expression is disrupted (e.g., because of the presence of a mutant Ph gene) the plants exhibit one or more of the following characteristics: 1) increased vacuolar pH as determined using the assays described below; 2) flower color shift from red toward blue as a result of pH effect on anthocyanin pigments; 3) enhanced fading of flower color with aging; and 4) appearance of seeds as shrivelled or irregularly shaped and less pigmented than wild-type. Such characteristics may also result from suppression of the Ph gene using suppression methods taught herein. In addition, allelism tests can be used to determine whether the mutant gene is capable of complementing a known Ph gene.

The Ph genes of the invention preferably encode proteins which affect the transcription of one or more genes encoding proteins affecting vacuolar pH. Typically, a Ph gene will encode a protein which is a transcriptional activator having a helix-loop-helix motif, as described below.

As used herein, a homolog of a particular Ph gene (e.g. the petunia Ph6 gene) is a second gene (either in the same plant type or in a different plant type) which has a polynucleotide sequence of at least 50 contiguous nucleotides which are substantially identical (determined as described above) to a sequence in the first gene. It is believed that, in general, homologs share a common evolutionary past.

The file of this patent contains at least one photograph executed in color. Copies of this patent with color photographs will be provided by the Patent and Trademark Office upon request and payment of the necessary fee.

BRIEF DESCRIPTION OF THE DRAWINGS

FIG. 2A shows hybridization to a probe made from the EcoRI-HindIII fragment of Ac. FIG. 2B shows hybridization to a probe made from the BstXI-EcoRI fragment flanking the Ac insertion.

FIG. 2A shows analysis of the somatic sector shown in FIG. 1B. Lane 1, 3057.12 parent plant; lanes 2 and 3, leaf and flower, respectively, borne on a variegated branch; lanes 4 and 5, leaf and flower, respectively, borne on a solidly colored branch. FIG. 3B is germinal revertants. Lane 1, V26 inbred line; lanes 2, 5, and 6, solidly colored progeny of a variegated plant; lanes 3 and 4, variegated progeny of same plant.

FIG. 5A shows Ph6/ph6 (top) and ph6-m1(Ac)/ph6 (bottom), both in a V26/W160 genetic background. FIG. 5B is a magnification of bottom flower in 5A showing the small revertant sectors on a mutant background.

FIG. 6A shows hybridization to the EcoRI-BamHI DNA fragment on the left side of the Ac insertion (FIG. 2C). FIG. 6B shows hybridization to the flower-specific CHS-A probe. FIG. 6C shows hybridization to a wheat rDNA probe. Lane 1, mutant leaf; lane 2, 2-cm mutant flower bud; lane 3, wild-type leaf; lane 4, 2-cm wild-type flower bud. Top arrow indicates the position of 28S rRNA; bottom arrow, position of 18S rRNA.

DESCRIPTION OF THE PREFERRED EMBODIMENTS

Figure 1A:
FIG. 1A shows a variegated petunia corolla produced by a plant homozygous for the ph6-m1(AC) allele.

The present invention provides compositions and methods for regulating vacuolar pH. The methods of the present invention may employ recombinant vectors comprising polynucleotide sequences from a Ph gene as described below. Ph genes useful in the present invention include Ph genes identified in petunia, as well as homologs in petunia and other plants (either of the same or different genus or species).

The effect of Ph genes on vacuolar pH has been elucidated by studying homozygous recessive alleles of these genes. For instance, in plants homozygous for the recessive allele of either the Ph1 or Ph2 gene (designated as ph1 and ph2) corolla pH is increased and the flowers have bluish color. In plants in which the ph3 gene is homozygous, corolla pH is increased, and female sterility is exhibited. If the ph4 gene is homozygous, the effects are similar to those of ph3, but the plants are fertile. Wiering et al., supra.

The Ph genes may also be associated with other flower color traits. For instance, it has been observed that flower color fades in some plants homozygous recessive for ph3 and ph4. Typically, about two to three days after the flower opens, anthocyanin begins to disappear and the flowers are completely white by the time they wither. Genetic experiments have shown that the fading trait is restricted to plants accumulating certain classes of anthocyanins. de Vlaming et al. *Theor. Appl. Genet.* 61:41–46 (1982).

The amino acid sequence in SEQ. ID. No. 2, as shown, comprises a helix-loop-helix structural motif starting with the sequence NHVLAER (starting at residue 191) and extending to the sequence KKVQDLE (ending at residue 244). Helix-loop-helix motifs are found in a number of eukaryotic genes and are thought to be involved in DNA binding during transcriptional activation. Proteins containing this motif include the myc family of oncogenes, regulators of neuron and muscle development, and regulators of segmentation and organ patterning in Drosophila. In plants, the motif is found in R(S), a protein involved with regulating anthocyanin synthesis in maize. Ludwig et al. *Proc. Natl. Acad. Sci. USA* 86:7092–7096 (1989). A comparison of the Ph6 and R(S) sequences over the 54 amino acid helix-loop-helix region performed by the BESTFIT program of GCG using standard parameters (gap weight: 3.000, length weight 0.100) detected 57% amino acid identity between the two proteins. Outside this region only 19% identity was found.

Without wishing to be bound by any particular theory, it is believed that, unlike previously described proteins encoded by transcriptional activators, the proteins encoded by the Ph genes of the invention specifically target a downstream gene or genes encoding proteins which control vacuolar Ph. That is, unlike ATPases and pyrophosphatases, the Ph proteins modulate vacuolar pH by regulating the expression of other proteins that directly affect vacuolar pH. Thus, the methods of the invention allow the control of vacuolar pH by suppressing or enhancing the expression of a single Ph gene, which in turn regulates the expression of one or more downstream genes.

Using the methods of the present invention vacuolar pH can be adjusted as desired. For instance, vacuolar pH may be increased or decreased by up to 1 pH unit or more, typically about 0.5 pH unit. Changes of 0.3 pH unit or less (e.g., 0.2 or 0.1 pH unit) may be desirably obtained. The changes in pH can be detected using the assays described below.

Any plant trait affected by vacuolar pH can be modified using the methods of the invention. Such modification may involve flowers, fruits or other plant parts. For instance, flower color of ornamental plants such as petunias, roses, carnations and the like can be modified. Storage properties of the fruit can also be improved by adjusting pH. Fruit acidity can be adjusted in fruits of various plants, e.g., citrus, tomato, grape, pineapple, tropical fruits (mango, passion fruit, papaya), berries (e.g., strawberry), melon, bananas, apples, pear, peach, apricot, nectarine, cherry, avocado, kiwi, and coffee. Also, the pH of other plant tissues, e.g. edible vegetable parts, can be modulated using these methods.

In general, the flavor of fruits depends upon the interaction of four classes of compounds: sugars, acids, non-volatile flavor compounds and volatile "aroma" compounds. The ratio of sugar:acid, in combination with specific flavor and aroma compounds, gives the unique flavor of any specific fruit. Flavor intensity is often determined more by the absolute levels of sugars and acids than by individual flavor compounds.

The flavor of many fruits, e.g., tomato or citrus fruits, is determined, in part, by acidity of cells of the fruit. The balance of sweetness and sourness is key to the flavor of a wide range of fruits, with the relative acidity of fruit determining the relative sourness. This has been shown by Stevens et al., *J. Amer. Soc. Hort. Sci.*, 104:40–42, (1979) in comparing a set of tomato lines. See also Sakiyama et al., *J. Amer. Soc. Hort. Sci.*, 101:394–96, (1976), and Picha, *HortScience,* 22:94–96, (1987) regarding tomato acidity. Stevens et al. also demonstrated that increasing acidity contributes to increasing intensity of tomato flavor. In tomato fruit, a range of pH values, from 4.0 to 5.0, is found among tomato varieties. In general, a lower fruit pH within that range gives better flavor intensity. The invention may be used to adjust fruit pH within known ranges or to move it outside those ranges.

The invention has use in altering pH-related traits in all higher plants, e.g., flavor (if edible), color or both. The invention thus has use over a broad range of types of plants, including species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyarmus, Lycopersicon, Nicotiana, Solanum, Petunia, Digitalis, Majorana, Ciahorium, Helianthus, Lactuca, Bromus, Asparagus, Antirrhinum, Hererocallis, Nemesis, Pelargonium, Panieum, Pennisetum, Ranunculus, Senecio, Salpiglossis, Cucumis, Browaalia, Glycine, Lolium, Zea, Triticum, Sorghum, and Datura.

More specifically, plants for which the invention may be used in modifying acidity-related traits (flower, color or otherwise) includes oil crops such as canola (*Brassica sp.*), cotton (*Gossypium sp.*), peanut (*Arachis sp.*), sunflower (*Helianthus sp.*), palm (*Elaeis sp.*), flax (*Linum sp.*), safflower (*Carthamus sp.*), coconut (*Cocos ap.*) and soybean (*Glycine sp.*); grain crops such as wheat (*Triticum sp.*), corn (*Zea sp.*), sorghum (*Sorghum sp.*), barley (*Hordeum sp.*), rye (*Secale sp.*), oats (*Avena sp.*) and rice (*Oryza sp.*); fruit crops such as banana (*Musa sp.*), citrus (*Citrus sp.*), berries (e.g., strawberry (*Fragaria Sp.*) or raspberry (*Rubus sp.*), mango (*Mangifera sp.*), melon (*Cucumis sp.*), pear (*Pyrus sp.*), cucumber (*Cucumis sp.*), and apricot, peach, cherry, plum and prune (*Prunus sp.*); vegetable crops such as pea (*Pisum sp.*), bean (*Vicia sp.*), broccoli and related crucifers (*Brassica sp.*), spinach (*spinacia sp.*), onion (*Allium sp.*), celery (*Apium sp.*), carrot (*Daucus sp.*), asparagus (*Asparagus sp.*), and artichoke (*Helianthus sp.*); additional ornamental crops such as tulip (*Tulipa sp.*), snapdragon (*Antirrhinum sp.*), Iris (*Iris sp.*), Orchids (*Cymbidium* and *Cattleya sp.*), *pelargonium*; beverage crops such as coffee (*Coffea sp.*) and tea (*Thea sp.*); herb crops such as mint (*Mentha sp.*), thyme (*Thymus sp.*) and marjoram (*origanum sp.*).

The control of the expression of genes associated with vacuolar pH, in particular Ph genes, can be achieved by introducing mutations into the gene or using recombinant DNA techniques. These techniques are generally well known to one of skill and are discussed briefly below.

Using the methods described below, the plants having the desired mutation (e.g., inhibited Ph gene expression) can be selected by assaying for changes in vacuolar pH. Thus, where the goal is inhibition of Ph gene expression plants having increased vacuolar pH are selected. Where overexpression of the Ph gene is desired plants having decreased vacuolar pH are selected. Alternatively, other desired phenotypic changes such as changes in pigmentation, as evidenced by e.g., modified flower color, can be used.

A number of methods are useful for introducing genetic mutations into a Ph gene. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Mutant plants or their progeny are then selected based on the desired altered phenotypes (resulting from mutations in Ph genes), such as flower color, fruit acidity, or pH of homogenized tissues using the assays described below. Mutation of the transcriptional activator sequence of a Ph6 gene can result in suppression of the downstream genes controlled by the Ph6 gene; Goff et al., *Genes & Dev,* 5:298–309 (1991).

The Example section below, which describes the isolation and characterization of the Ph6 gene in Petunia, is exemplary of a general approach for isolating Ph genes. Isolation of this gene allows one of skill to readily isolate homologous genes in Petunia and other plant species. The isolated genes can then be used to construct recombinant vectors for altering Ph gene expression in transgenic plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989), which is incorporated herein by reference.

The isolation of Ph genes may be accomplished by a number of techniques. For instance, transposon tagging of a Ph gene can assist in the isolation of the relevant gene. Transposon tagging involves introducing a transposon into the plant which leads to a mutation of the target gene and a detectable phenotypic change in the plant. Using a probe for the transposon, the mutant gene can then be isolated. Using the DNA adjacent to the transposon in the isolated mutant gene as a probe, the normal wild type allele of the target gene can be isolated. See, e.g., Haring, et al., *Plant Mol. Biol.* 16:449–469 (1991) and Walbot, *Ann. Rev. Plant Mol. Biol.* 43:49–82 (1992). As shown below, a particularly useful transposon tagging system is that disclosed in U.S. Pat. No. 5,013,658, which is incorporated herein by reference.

An alternative method uses oligonucleotide probes to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as a flower, and a cDNA library which contains the Ph gene transcript is prepared from the mRNA. Alternatively, cDNA may be prepared from mRNA extracted from other tissue types (organs) in which Ph genes or homologs are expressed such as seeds, fruits, leaves, stems, and roots.

The cDNA or genomic library can then be screened using a probe based upon the sequence of a cloned Ph gene such as Ph6. Probes may be used to hybridize with genomic DNA or cDNA sequences to isolate homologous genes in the same or different plant species. The use of such hybridization techniques for identifying homologous genes is well known in the art and need not be described further.

Alternatively, polynucleotides may be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983), both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

The isolated sequences prepared as described herein, can be used in a number of techniques to suppress endogenous Ph gene expression (i.e., to raise the pH and thus lower acidity). For instance, antisense technology can be conveniently used to inhibit Ph gene expression. To accomplish this, a nucleic acid segment from the desired gene is cloned and operably linked to a promoter such that the anti-sense strand of RNA will be transcribed. The construct is then transformed into plants and the anti-sense strand of RNA is produced. In plant cells, it has been shown that anti-sense RNA inhibits gene expression by preventing the accumulation of mRNA which encodes the enzyme of interest, see, e.g., Sheehy et al., *Proc. Nat. Acad. Sci. USA,* 85:8805–8809 (1988), and Hiatt et al., U.S. Pat. No. 4,801,340 which are incorporated herein by reference.

The nucleic acid segment to be introduced generally will be substantially identical to at least a portion of the endogenous Ph gene or genes to be repressed. The sequence, however, need not be perfectly identical to inhibit expression. The vectors of the present invention can be designed such that the inhibitory effect applies to other proteins within a family of genes exhibiting homology or substantial homology to the target gene. For example, suppression of the Ph6 gene may serve to impose the same suppressive effect on other Ph genes with sufficient identity. Similarly, segments from Ph genes from Petunia can be used to inhibit expression of homologous genes in different plant species, e.g., using sense or antisense suppression techniques described herein either directly or as a means to obtain the corresponding sequences to be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of Ph genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988), which is incorporated herein by reference.

Another method of suppression is sense suppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. No. 5,034,323, which are incorporated herein by reference.

Generally, where inhibition of expression is desired, some transcription of the introduced sequence must occur. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

The introduced sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Isolated sequences prepared as described herein can also be used to enhance or increase endogenous Ph gene expression (i.e., to lower the pH and thus raise acidity). Where overexpression of the Ph gene is desired, a Ph gene from a different species may be used to decrease potential sense suppression effects. For instance, the petunia Ph6 gene can be used to increase expression in tomato fruit.

One of skill will recognize that the polypeptides encoded by the Ph genes, like other proteins, have different domains which perform different functions. Thus, the Ph gene sequences need not be full length, so long as the desired functional domain of the protein is expressed. Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

To use isolated Ph sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988), which is incorporated herein by reference. A DNA sequence coding for the desired Ph polypeptide, for example a cDNA sequence encoding a full length protein, will be combined with transcriptional and translational initiation regulatory sequences which will direct the transcription of the sequence from the Ph gene in the intended tissues of the transformed plant.

For example, a plant promoter fragment may be employed which will direct expression of the Ph in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens,* and other transcription initiation regions from various plant genes known to those of skill.

Alternatively, the plant promoter may direct expression of the Ph gene in a specific tissue or may be otherwise under more precise environmental or developmental control. Such promoters are referred to here as "inducible" promoters. Examples of environmental conditions that may effect transcription by inducible promoters include anaerobic conditions or the presence of light.

Examples of promoters under developmental control include promoters that initiate transcription only in certain tissues, such as fruit, seeds, or flowers. For example, the use of a polygalacturonase promoter can direct expression of the Ph polypeptide in the fruit, a CHS-A (chalcone synthase A from petunia) promoter can direct expression of the Ph polypeptide in flower of a plant.

If proper polypeptide expression is desired, a polyadenylation region at the 3'-end of the Ph coding region should be included. The polyadenylation region can be derived from the natural gene, from a variety of other plant genes, or from T-DNA.

The vector comprising the sequences from a Ph gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulforon or Basta.

Such DNA constructs may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987). The full disclosures of each of these references are incorporated herein by reference.

*Agrobacterium tumefaciens*-mediated transformation techniques are well described in the scientific literature. See, for example Horsch et al. *Science* 233:496–498 (1984), and Fraley et al. *Proc. Natl. Acad. Sci. USA* 80:4803 (1983), all of which are incorporated herein by reference.

Transformed plant cells which are derived by any of the above transformation techniques can be cultured to regenerate a whole plant which possesses the transformed genotype and thus the desired Ph-controlled phenotype. Such regeneration techniques rely on manipulation of certain phytohormones in a tissue culture growth medium, typically relying on a biocide and/or herbicide marker which has been introduced together with the Ph nucleotide sequences. Plant regeneration from cultured protoplasts is described in Evans et al., *Protoplasts Isolation and Culture, Handbook of Plant Cell Culture,* pp. 124–176, MacMillilan Publishing Company, New York, 1983; and Binding, *Regeneration of Plants, Plant Protoplasts,* pp. 21–73, CRC Press, Boca Raton, 1985, all of which are incorporated herein by reference. Regeneration can also be obtained from plant callus, explants, organs, or parts thereof. Such regeneration techniques are described generally in Klee et al. *Ann. Rev. of Plant Phys.* 38:467–486 (1987), which is incorporated herein by reference.

The methods of the present invention are particularly useful for incorporating the Ph genes into transformed plants in ways and under circumstances which are not found naturally. In particular, the Ph polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The effect of the modification of Ph gene expression is conveniently detected by measuring vacuolar pH. Vacuolar pH can be measured using conventional assay techniques. For example, corolla pH can be detected by using pH meter to measure pH in fresh flower tissue homogenized in water as described by de Vlaming et al., supra.

In the case of desired modifications to flower color, inhibition of Ph gene expression can be detected by a change in anthocyanin pigmentation from red to blue. In addition, antisense or sense suppression of the endogenous gene can be detected by reduction of mRNA levels as measured by, for instance, Northern blots.

The following Examples are offered by way of illustration, not limitation.

EXAMPLES

I. Isolation of a Variegated Flower Color Mutation in a Petunia Line Carrying Ac This Example describes the generation of independent transformants carrying the Ac transposable element in Petunia. The stain used here, V26, a highly inbred, purple-flowered genetic line was obtained from the collection at the Free University of Amsterdam.

The binary vector used in transformation, pJJ4411, was constructed generally as described in U.S. Pat. No. 5,013,658. The vector was constructed as described in Keller et al., *Plant Mol. Biol.* 21:157–170 (1993), which is incorporated herein by reference.

In addition to a hygromycin resistance transformation marker, this vector contains the streptomycin phosphotransferase (SPT)::Ac excision marker between the right and left T-DNA borders. The maize element Ac interrupts the SPT gene and prevents its expression. In several plants, such as tobacco and Arabidopsis, this marker is a useful visual indicator of somatic and germinal Ac activity. In petunia, however, the streptomycin germination screen is not as reliable. It can be used to enrich for plants carrying transposed Ac elements (trAcs). This procedure results in a greater than 10-fold enrichment for trAcs in petunia.

One of the analyzed plants (3057.12) carried two Ac elements in heterozygous condition. One Ac element was still in its resident site in a T-DNA and the other at an unlinked chromosomal location, into which it had integrated following a secondary transposition event from a different T-DNA. Plant 3057.12 was selfed in order to make homozygous the transposed Ac (trAc) element and, therefore, any mutation caused by the trAc insertion.

When the self-progeny was planted, a new, variegated flower color phenotype was found to segregate as a simple recessive Mendelian trait. As can be seen in FIG. 1A, the variegated flower phenotype is striking. In the flowers, darkly colored (revertant) sectors, outlined by white rims, stand out sharply against the pale colored (mutant) background of the corolla. The color of the background and the revertant sectors varies depending on the residual genotype. In segregants from outcrosses to other genetic lines, the background color is blue and the revertant color red. In all flowers, a white rim separates the revertant sector from the mutant background.

Borders of different colors are rarely seen in examples of anthocyanin variegation. When they are seen, the rims tend to be more, not less, pigmented than the areas they delimit. The formation of new anthocyanin pigments in the border cells has been attributed to the diffusion of accumulated intermediates from adjacent cells. The presence of white rims in the variegated flowers of the plants of the present invention suggests that compounds can diffuse into the border cells from adjacent cells, i.e., that the effect of the mutated gene on anthocyanin pigmentation is not strictly cell autonomous.

II. Evidence That the New Mutation is Tagged by Ac

The following evidence indicates that the new variegated mutation has arisen as a consequence of an Ac transposition event, and was, therefore, tagged by Ac.

A. Cosegregation with Ac-hybridizing band

The mutation cosegregated with a new Ac-hybridizing band in DNA gel blots of the self progeny of plant 3057.12. DNA from the variegated (mutant) and solidly colored (parental) progeny was analyzed by digestion with different enzymes and hybridization with an Ac probe. To do this, genomic DNA (6 µg) was digested with the enzyme, separated by electrophoresis on a 1% agarose gel, and transferred to a nylon membrane according to standard techniques.

Figure 2A:
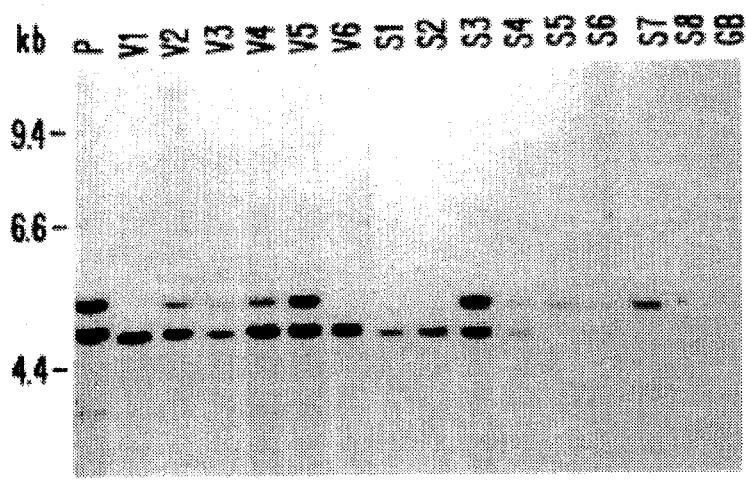
FIGS. 2A and 2B show DNA gel blot analysis of variegated and solidly colored progeny of plant 3057.12, carrying a trAc element. P indicates the 3057.12 parent; V1 to V6, variegated progeny; S1 to S8, solidly colored progeny; GB, nontransgenic plant of V26 genetic background. Molecular length markers are given at left in kilobases.

As seen in the genomic DNA gel blot shown in FIG. 2A, in an EcoRI digest a new Ac-hybridizing band was found that cosegregated with the new variegated phenotype. In particular, a 4.7-kb band was present in every variegated plant (V1–V6), but only in some solidly colored siblings (S1, S2 and S3). The larger (5-kb) band represents the second unlinked Ac element. This band can be seen to segregate in both the variegated and the solidly colored siblings.

Among those variegated plants that received both Ac fragments, the intensity of the 4.7-kb band relative to the 5-kb band is either the same (V5) or double (V2, V3 and V4), suggesting that the new, 4.7-kb band is homozygous but that the 5-kb band can be either homozygous (V5) or heterozygous (V2, V3, V4). Conversely, some solidly colored progeny (S3 and S7) appear to be homozygous for the 5-kb, but not the 4.7-kb band.

In all, 26 variegated siblings were analyzed and all showed the new, Ac-hybridizing band at about the same relative intensity. Of 25 solidly colored siblings analyzed, 16 had the 4.7-kb band, a result in agreement with the proportion of heterozygotes for the new mutation (two thirds) expected within the solidly colored class. These data indicate that the new mutation is linked to the trAc band ($\chi^2$=10.2, P<0.01). Though no recombinants were found in the self progeny, the resolution of this type of F2 linkage data (repulsion phase, complete dominance) is limited, so the 95% confidence interval for the estimate of p, the recombination fraction, is large (p=0; CI=0–0.34).

B. Homozygosity for the Ac-tagged fragment

All the mutant plants were homozygous for the Ac tagged DNA fragment. The Ac homologous, 4.7-kb EcoRI fragment, containing part of Ac and DNA adjacent to the Ac insertion, was cloned into the vector λZapII (Stratagene). A restriction map of this fragment (and of the adjacent 6.8-kb EcoRI fragment subsequently isolated) is shown in FIG. 2C. The BstXI-EcoRI fragment flanking Ac in the 4.7-kb Ac fragment was labeled and used to reprobe the blot shown in FIG. 2A. If the variegated plants are indeed homozygous for the new, 4.7-kb Ac band, they should lack the allelic wild-type fragment, which, conversely, should be present in all of the solidly colored siblings.

Figure 2B:
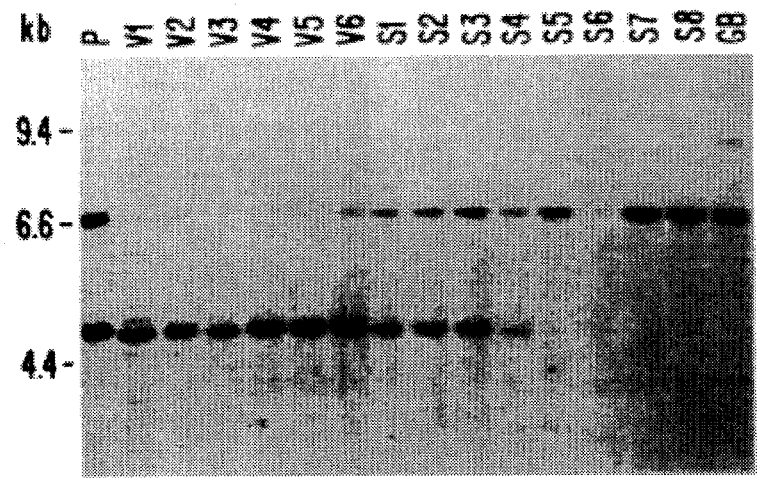
Figure 2C:
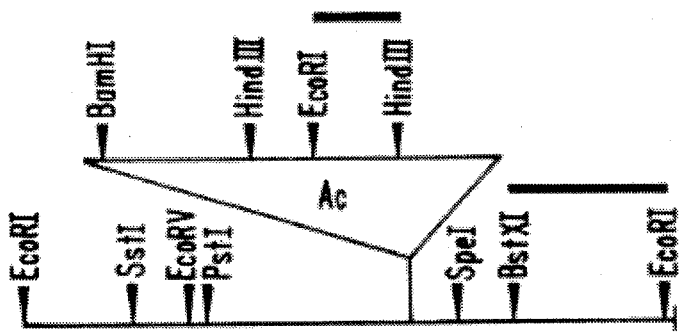
FIG. 2C shows a restriction map of Ph6 DNA mutated by insertion of Ac. The positions of the probes corresponding to Ac and to the flanking DNA are indicated by bars above the map.

The DNA gel blot presented in FIG. 2B confirms this. The solidly colored progeny show a 7-kb band of identical mobility to the band seen in the wild-type V26 inbred parent. In contrast, the variegated siblings either lack that band or show it at a very reduced intensity. The weak band present in the variegated progeny can be attributed to occasional somatic excisions of Ac.

Those solidly colored progeny that did not show a 4.7-kb Ac homologous band in FIG. 2A are homozygous for the V26 wild-type fragment. Solidly colored progeny that did show a 4.7-kb Ac homologous band are heterozygous for the V26 fragment.

The overall segregation obtained from having scored the progeny of plant 3057.12 with the two different probes (Ac and its flanking sequence) is as follows. Among the 25 solidly colored progeny analyzed, 16 were Ac/+, 9 were +/+, and none were Ac/Ac. Among the 26 variegated progeny, all were Ac/Ac. This more complete genotypic classification of the F2 progeny significantly reduces the size of the 95% confidence interval for p (p=0; CI=0–0.05) and demonstrates that the new mutation is, in fact, closely linked to Ac.

C. Reversion to wild-type phenotype

Figure 1B:
FIG. 1B shows a plant with a variegated mutant flower (bottom) and solidly colored revertant flower (top).

Reversion of the mutation to the wild-type phenotype was correlated with restoration of a wild-type sized DNA fragment. Confirmation that a mutation is, in fact, tagged by Ac can be sought from an analysis of revertants because an excision of Ac that restores the wild-type phenotype should also produce a DNA fragment of the original wild-type size. Progeny from variegated plants were grown and screened for somatic and germinal reversion events. Branches with solidly colored flowers, representing large somatic revertant sectors, were occasionally seen on plants producing mostly variegated flowers (FIG. 1B). DNA from the solidly colored and variegated branches of one such plant was prepared and analyzed by DNA gel blotting.

Figure 3A:
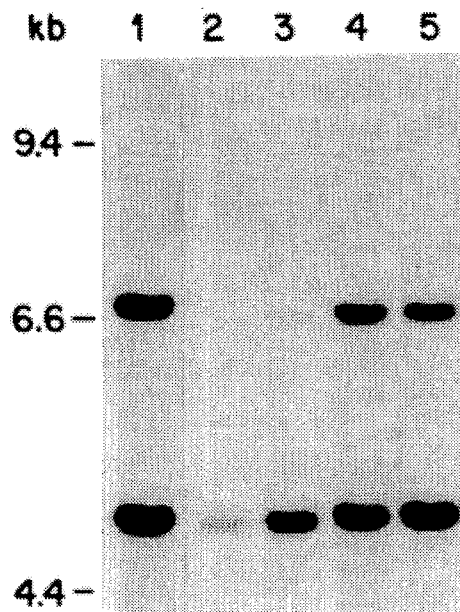
FIGS. 3A and 3B are DNA gel blot analyses of revertants. The blot was probed with the BstXI-EcoRI fragment from DNA flanking the Ac insertion (bar in FIG. 2C). Molecular length markers are given at left in kilobases.

The blot shown in FIG. 3A was probed with the BstXI-EcoRI DNA fragment flanking Ac (FIG. 2C). Two bands of roughly equal intensity can be seen in the lanes containing DNA from a flower and a leaf that were borne on a revertant branch (lanes 4 and 5). One is a 7-kb, wild-type-sized band and the other, a 4.7-kb band, which also hybridizes to Ac (data not shown). This observation indicates that the revertant sectors are heterozygous for the original Ac-induced mutation and a revertant allele produced by excision of Ac during development of the chimeric plant. Capsules borne on the revertant branches produced solidly colored and variegated individuals in a 3:1 ratio, confirming that the reversion event was heritable. The lanes containing DNA from a flower and leaf that were borne on a variegated branch (FIG. 3A, lanes 2 and 3) show, in contrast, a strong 4.7-kb Ac band and a faint 7-kb band. The latter band probably represents empty sites generated by somatic excisions of Ac during the formation of the variegated flower. Capsules borne on variegated branches produced, as expected, mostly variegated progeny.

Plants with only solidly colored flowers were obtained among the progeny of variegated plants at frequencies ranging from 6 to 27%, indicating that the new mutation is also germinally unstable and reverts frequently to the wild-type state. Representative reversion data are shown in Table 1.

TABLE 1

| | | Frequency of germinal revertants | | |
|---|---|---|---|---|
| Family | Pedigree | Number variegated plants | Number solid plants | Frequency germinal revertants[a] |
| 3426 | V26xM59 | 73 | 9 | 0.11 |
| 3428 | V26xM59 | 103 | 25 | 0.19 |
| 3434 | V26xM59 | 35 | 13 | 0.27 |
| 3466 | V26xM59 | 51 | 9 | 0.15 |
| 3429 | V26 | 22 | 2 | 0.08 |
| 3468 | V26 | 91 | 6 | 0.06 |

[a]Number of solidly colored plants to total number of plants.

Figure 3B:
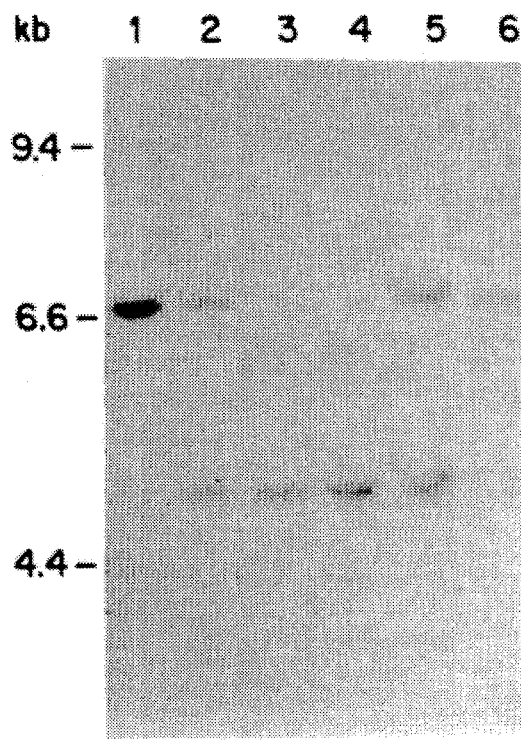

Ten independent germinal revertants were analyzed by DNA gel blots, confirming the observations made earlier for the somatic revertant sectors. FIG. 3B illustrates the analysis of three such germinal revertants. All the revertants (lanes 2, 5, and 6) showed the 7-kb, wild-type-sized band in addition to the 4.7-kb band. They are, therefore, heterozygous for a revertant allele and the original Ac-induced mutation. The segregating variegated siblings (FIG. 3B, lanes 3 and 4), on the other hand, showed only the 4.7-kb band; they are homozygous for the Ac mutation, consistent with their phenotype. In addition, six of eight revertants analyzed had new Ac bands, indicating that the excised Ac elements continue to be capable of reinsertion.

The above evidence shows that the new variegated petunia mutant arose from the transposition of the maize element Ac into a gene affecting flower color.

III. The gene tagged by AC affects the acidity of the corolla

Several considerations suggested that the new Ac-tagged mutant was a mutation of a Ph gene. First, in certain genetic backgrounds, the revertant sectors in the variegated flowers appear red, whereas the mutant background has a distinct bluish hue. This color change is reminiscent of that brought about by the Ph mutations described above which cause a bluing of the corolla by increasing the vacuolar pH in the anthocyanin-accumulating cells (Viering et al., supra). Anthocyanins in solution undergo a similar shift from red to blue as the acidity decreases.

Second, the new mutation affects the pH of the corolla in a manner similar to the known Ph mutant ph1. This was established by comparing the corolla pH of mutant and revertant plants that arose in the self-progeny of a variegated plant, which was also Hf1 Ph1/hf1 ph1. Hf1 and Ph1 are closely linked genes on chromosome 1 that affect pigmentation of the corolla. Hf1 controls hydroxylation at the 5' position of the anthocyanin B ring and causes a bluing of the corolla. Ph1 increases acidity in the vacuoles of the corolla and produces a more reddish hue.

The Hf1 Ph1/hf1 ph1 heterozygote was obtained from an outcross of a variegated V26 plant (Hf1 Ph1) to line M59 (hf1 ph1). Among Hf1 segregants, the pH of the corolla was higher in the mutant plants (5.89±0.02) than in the revertant plants (5.57±0.03), a result that suggested that the new mutation altered the acidity of the corolla. This increase in pH can be compared to that caused by the ph1 mutation in the same segregating family. Because ph1 and hf1 are only 1 centimorgan apart, hf1 segregant should also be ph1/ph1 and, therefore, were used to compare the effects on corolla pH of ph1 and of the new mutation. Two revertant progeny of the hf1 class (and, presumably, ph1/ph1) were recovered, and both had high corolla pH values (5.90±0.05), similar to those measured in the variegated flowers of the Hf1 class.

Figure 1C:
FIG. 1C shows a branch showing an older variegated flower (left) with a faded background color relative to that of the recently opened variegated flower (right).

Third, in some variegated plants the color of the flower fades with aging (FIG. 1C), a phenomenon that has also been observed in petunia lines carrying certain ph mutations in conjunction with the Fa allele as described above (de Vlaming et al., supra). The pigments present in the faded corollas of the variegated line were compared with those present in the faded corollas of a ph4 mutant line. In both cases, the faded flowers accumulated a phenolic compound fluorescing blue under ultraviolet light. This compound was absent in extracts of recently opened, nonfaded, flowers.

Figure 4:
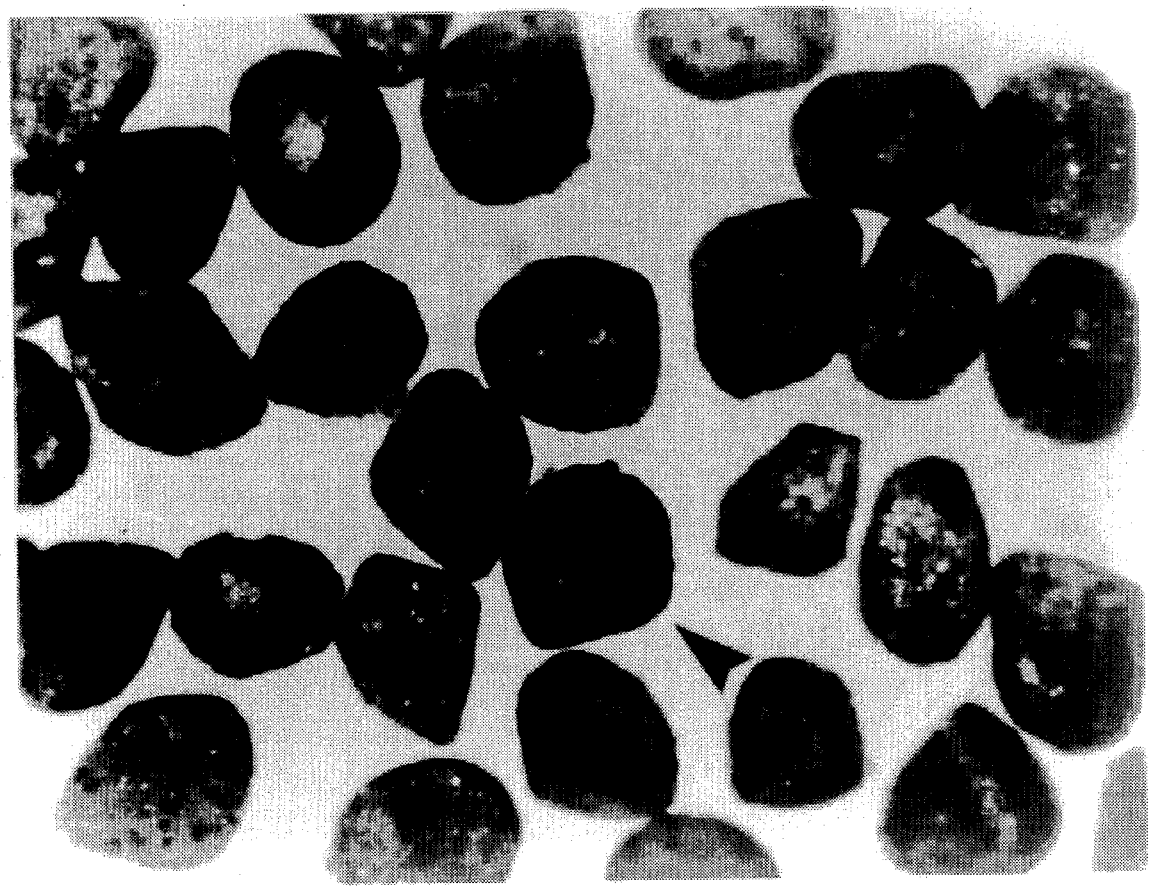
FIG. 4 shows seeds produced by the ph6-m1(Ac) mutation. The pigmented seed indicated by the arrow looks normal and probably arose as a consequence of an Ac excision event early in seed coat development.

Fourth, the new mutation has a pleiotropic effect on seed development, an effect that has also been associated with some ph mutations (Viering, supra). When examined under 30× magnification, seeds borne on mutant plants appear abnormal. Some are shrivelled or irregularly shaped and the vast majority are variegated. The seed coat of normal petunia seeds is uniformly pigmented and reticulated. As shown in FIG. 4, the mutant seed coat is largely unpigmented and lacks the honeycomb network of normal seeds, except for areas of varying size where the pigmented and reticulated peripheral structure is restored. The variegated seed phenotype of the Ac-induced mutation can be readily explained as another manifestation of somatic instability: the normal sectors on the mutant seed coats would form as a result of Ac excisions that occurred during seed development.

Figure 5A:
FIGS. 5A and 5B show flower phenotypes from the allelism test to ph6.
Figure 5B:
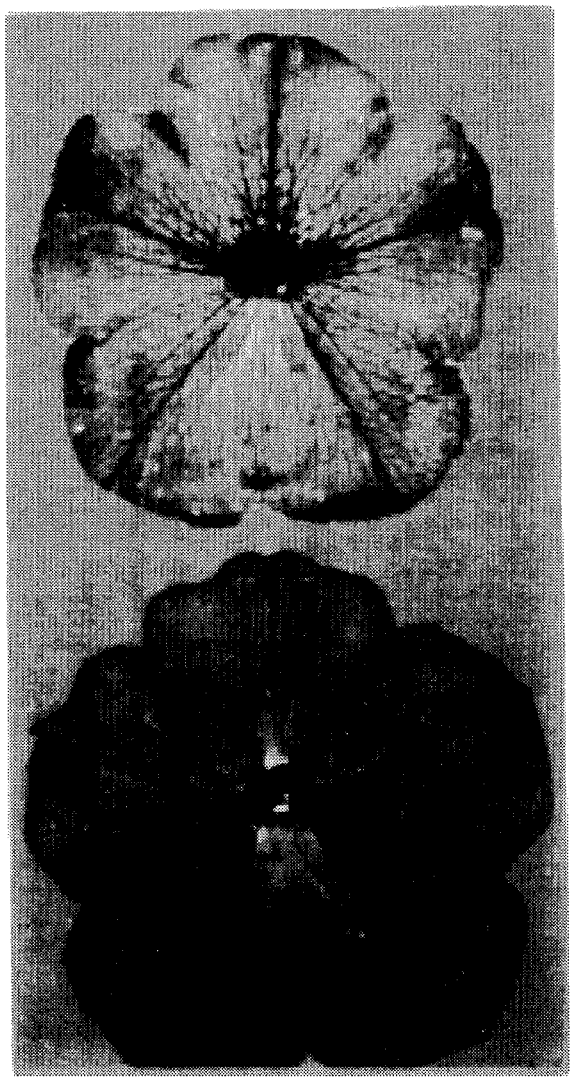

The observations given above cumulatively suggested that Ac had become inserted in one of the Ph genes. Allelism tests were conducted with known ph mutants to establish that the variegated mutant was capable of complementing all the mutants tested, except for ph6, as illustrated in FIG. 5. The new, Ac-tagged ph6 mutation was designated ph6-m1(Ac). The petunia line carrying the standard ph6 mutation used in the complementation test is W160. (Available from the collection at the Free Univ. of Amsterdam).

The flower phenotype conditioned by the ph6-m1(Ac) allele in outcrosses to W160 is clearly different from that produced in the pure V26 line or in a mixed V26/M59 genetic background. Only small sectors can be seen (FIG. 5) due to reversion events that occur late in flower development. The seed phenotype is similarly affected: a few of the seeds borne on the outcross plants show traces of pigmentation, but the majority are unpigmented.

Figure 6A:
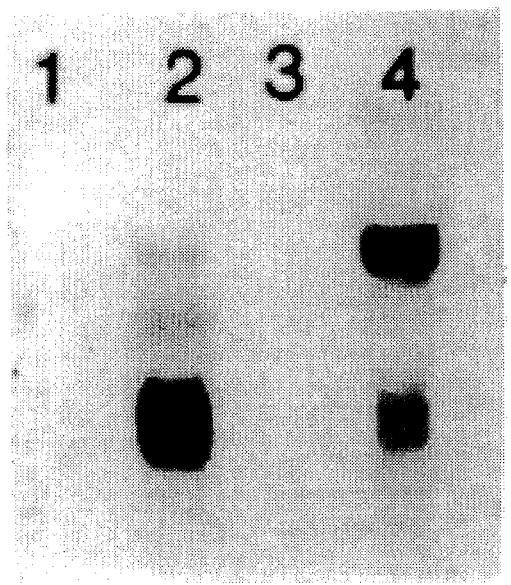
FIGS. 6A–6C is a RNA gel blot of wild-type and mutant flower buds and leaves hybridized sequentially to three probes.

IV. The ph6-m1(Ac) mutation encodes an altered form of a flower-specific transcript To detect a Ph6 transcript, total RNA was prepared from Ph6 and ph6-m1(Ac) flower buds and leaves. The RNAs were separated on a 1.1% agarose gel, blotted onto a nylon membrane, and probed with the EcoRI-BamHI fragment that extends from the BamHI site in Ac to the left of the insertion site (FIG. 2C). The corresponding RNA gel blot is shown in FIG. 6A. An approximately 2.8-kb transcript was detected in wild-type flower buds (lane 4). In the mutant flower bud (lane 2), only a trace of the 2.8-kb transcript can be seen; the major signal is given, instead, by a 2-kb transcript. Possibly, alternate splicing caused by the Ac insertion accounts for the multiple transcripts seen in the mutant (Wessler, 1988). No transcript was detected in either mutant or wild-type leaves (lanes 1 and 3), suggesting that the Ph6 gene is expressed preferentially in flowers.

Figure 6B:
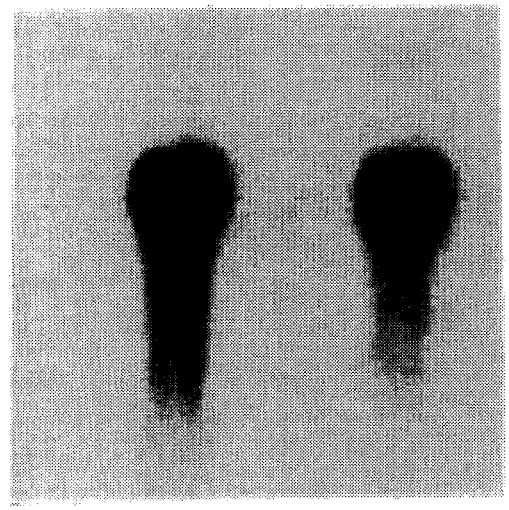

The RNA gel blot was rehybridized with the petunia flower-specific chalcone synthase probe CHS-A (Koes et al., *Plant Mol. Biol.* 12:213–225 (1989)) after washing away the first probe (FIG. 6B). Transcripts of the same size and intensity were detected in mutant and wild-type flower buds (lanes 2 and 4, respectively), but not in mutant and wild-type leaves (lanes 1 and 3, respectively). This result shows that the mutant RNA sample was not degraded and confirms the flower-specific nature of the Ph6 transcript.

Figure 6C:
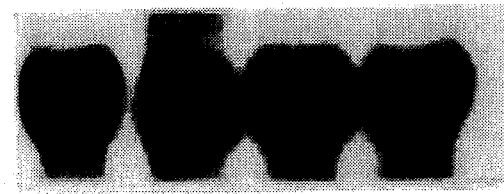

FIG. 6C shows the comparable 28S rRNA signal given by the four RNA samples when the RNA gel blot was rehybridized with a wheat rDNA probe, confirming that the four lanes were loaded with approximately the same amount of RNA.

V. Isolation of Ph6 DNA

Poly(A) RNA was isolated from total RNA from flower buds (Example IV above) and used to generate a cDNA library in the vector lambda ZapII (Stratagene). The SstI to BamHI fragment at the left hand side of Ac in FIG. 2c was used to isolate pPet14-1 (containing a partial Ph6 cDNA) the sequence for which is given in SEQ. ID No. 1. Sequencing was via dideoxy sequencing using a Promega kit. Comparison of sequence information from the cDNA clone pPet14-1, and from the 4.7 and 6.8 Kb genomic clones described in Example IIB above was used to confirm that the Ac element had disrupted Ph6 by insertion within the gene, and also to show that the Ph6 gene is a transcriptional regulator.

Although the foregoing invention has been described in detail for purposes of clarity of understanding, it will be obvious that certain modifications may be practiced within the scope of the appended claims.

What is claimed is:

1. An isolated DNA construct comprising a polynucleotide sequence of at least about 30 nucleotides from a Ph6 gene.

2. The DNA construct of claim 1, wherein the Ph6 gene controls expression of a gene encoding a protein which regulates vacuolar pH.

3. The DNA construct of claim 2, wherein the Ph6 gene encodes a protein having a helix-loop-helix motif.

4. The DNA construct of claim 1, wherein the Ph6 gene is from petunia.

5. The DNA construct of claim 1, wherein the polynucleotide sequence encodes a polypeptide having a sequence as shown in SEQ. ID. No. 2.

6. The DNA construct of claim 1, wherein the polyucleotide sequence is SEQ. ID. No. 1.

7. The DNA construct of claim 1, wherein the polynucleotide sequence is a full length Ph6 gene.

8. The DNA construct of claim 1, further comprising a promoter operably linked to the polynucleotide sequence.

9. The DNA construct of claim 8, wherein the polynucleotide sequence is linked to the promoter in an antisense orientation.

10. The DNA construct of claim 8, wherein the promoter is a plant promoter.

11. The DNA construct of claim 10, wherein the promoter is a fruit-specific promoter.

12. The DNA construct of claim 10, wherein the promoter is a flower-specific promoter.

13. A transgenic plant comprising a recombinant expression cassette comprising a plant promoter operably linked to a polynucleotide sequence of at least about 30 nucleotides from a Ph6 gene.

14. The transgenic plant of claim 13, wherein the plant promoter is a heterologous promoter.

15. The transgenic plant of claim 13, wherein the polynucleotide sequence is linked to the promoter in an antisense orientation.

16. The transgenic plant of claim 13, wherein the plant is petunia.

17. The transgenic plant of claim 13, wherein the polynucleotide sequence is SEQ. ID. No. 1.

18. A method of altering vacuolar pH in a plant, the method comprising:

introducing into plant tissue a recombinant expression cassette comprising a plant promoter operably linked to a polynucleotide sequence from a Ph6 gene;

regenerating the plant tissue into a whole plant, whereby the regenerated plant transcribes the polynucleotide sequence; and selecting plants having altered vacuolar pH.

19. The method of claim 18, wherein the plant tissue is from petunia, rose or tomato.

20. The method of claim 18, wherein the recombinant expression cassette is introduced into the plant tissue using Agrobacterium.

21. The method of claim 18, wherein the polynucleotide sequence is linked to the promoter in an antisense orientation.

22. The method of claim 18, wherein the polynucleotide sequence is linked to the promoter in a sense orientation.

23. The method of claim 18, wherein the polynucleotide sequence is SEQ. ID. No. 1.

24. The method of claim 18, wherein the promoter is a fruit-specific promoter.

25. The method of claim 18, wherein the promoter is a flower-specific promoter.

26. A method of isolating a Ph gene from a plant, the method comprising probing a DNA library prepared from the plant with oligonucleotide probes comprising a polynucleotide sequence from an isolated Ph6 gene.

27. The method of claim 26, wherein the DNA library comprises cDNA.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1149 base pairs
( B ) TYPE: nucleic acid
( C ) STRANDEDNESS: single
( D ) TOPOLOGY: linear ( i i ) MOLECULE TYPE: cDNA ( i x ) FEATURE:
 ( A ) NAME/KEY: CDS
 ( B ) LOCATION: 1..1146

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CAG | CTT | GAT | ATG | TCT | GAG | GCA | ATA | CGG | TTT | GGG | TCA | CCG | GAT | GAC | GGC | 48 |
| Gln | Leu | Asp | Met | Ser | Glu | Ala | Ile | Arg | Phe | Gly | Ser | Pro | Asp | Asp | Gly | |
| 1 | | | | 5 | | | | | 10 | | | | | 15 | | |
| TCC | AAT | ACA | AAT | ATG | GAC | TCT | GAT | TTC | CAT | ATG | GTT | GGA | GTT | AGC | CAA | 96 |
| Ser | Asn | Thr | Asn | Met | Asp | Ser | Asp | Phe | His | Met | Val | Gly | Val | Ser | Gln | |
| | | | 20 | | | | | 25 | | | | | 30 | | | |
| GCC | GAA | AAC | CCA | GCT | GAC | TAC | CAG | CGC | CAA | GCT | GAG | TCA | TTC | AAA | GCT | 144 |
| Ala | Glu | Asn | Pro | Ala | Asp | Tyr | Gln | Arg | Gln | Ala | Glu | Ser | Phe | Lys | Ala | |
| | | 35 | | | | | 40 | | | | | 45 | | | | |
| GAC | ACT | TCC | ATT | AGC | TGG | GCT | CAT | TTC | CAA | GAC | CTT | CCA | CAT | TTA | CCA | 192 |
| Asp | Thr | Ser | Ile | Ser | Trp | Ala | His | Phe | Gln | Asp | Leu | Pro | His | Leu | Pro | |
| | 50 | | | | | 55 | | | | | 60 | | | | | |
| GGC | GGC | CCT | AGT | TAT | GAT | GAA | TTA | TCA | CAA | GAA | GAC | ACA | CAT | TAC | TCT | 240 |
| Gly | Gly | Pro | Ser | Tyr | Asp | Glu | Leu | Ser | Gln | Glu | Asp | Thr | His | Tyr | Ser | |
| 65 | | | | | 70 | | | | | 75 | | | | | 80 | |
| CAA | ACA | GTG | TCG | ACC | ATT | CTT | GAA | CAC | CTC | TCA | AAC | CAA | AGC | TCC | AAA | 288 |
| Gln | Thr | Val | Ser | Thr | Ile | Leu | Glu | His | Leu | Ser | Asn | Gln | Ser | Ser | Lys | |
| | | | | 85 | | | | | 90 | | | | | 95 | | |
| TTT | TCC | TCT | ACC | ATA | ATG | GGC | TGT | ATT | TCC | CAA | ACA | ACC | CAA | TCT | GCC | 336 |
| Phe | Ser | Ser | Thr | Ile | Met | Gly | Cys | Ile | Ser | Gln | Thr | Thr | Gln | Ser | Ala | |
| | | | 100 | | | | | 105 | | | | | 110 | | | |
| TTC | ACA | AGG | TGG | CCC | AGC | CCC | AGC | ACC | ACC | GTC | TCC | AGC | CCA | TTT | CTT | 384 |
| Phe | Thr | Arg | Trp | Pro | Ser | Pro | Ser | Thr | Thr | Val | Ser | Ser | Pro | Phe | Leu | |
| | | 115 | | | | | 120 | | | | | 125 | | | | |
| GAC | GGC | GGC | GCC | ACC | TCC | GGC | CAG | TGG | CTG | CTC | AAA | AGC | ATA | CTA | TTC | 432 |
| Asp | Gly | Gly | Ala | Thr | Ser | Gly | Gln | Trp | Leu | Leu | Lys | Ser | Ile | Leu | Phe | |
| | 130 | | | | | 135 | | | | | 140 | | | | | |
| TCT | GTT | CCA | TTT | CTT | CAC | ACT | AAA | TAC | CAA | ACT | GCA | GCT | GAA | GTT | TCT | 480 |
| Ser | Val | Pro | Phe | Leu | His | Thr | Lys | Tyr | Gln | Thr | Ala | Ala | Glu | Val | Ser | |
| 145 | | | | | 150 | | | | | 155 | | | | | 160 | |
| CCA | AAG | TCA | CGT | GAC | GCT | ACC | ACT | GTT | GAT | TCC | TCC | ACT | GCA | TCT | CGC | 528 |
| Pro | Lys | Ser | Arg | Asp | Ala | Thr | Thr | Val | Asp | Ser | Ser | Thr | Ala | Ser | Arg | |
| | | | | 165 | | | | | 170 | | | | | 175 | | |
| TTT | CGA | AAA | GGG | TGT | AGT | ATA | ACA | CAA | GAA | GAG | CCT | AGT | GGA | AAC | CAT | 576 |
| Phe | Arg | Lys | Gly | Cys | Ser | Ile | Thr | Gln | Glu | Glu | Pro | Ser | Gly | Asn | His | |
| | | | 180 | | | | | 185 | | | | | 190 | | | |
| GTA | CTT | GCT | GAA | CGA | CGG | CGT | AGA | GAA | AAG | CTC | AAC | GAA | CGG | TTT | ATC | 624 |
| Val | Leu | Ala | Glu | Arg | Arg | Arg | Arg | Glu | Lys | Leu | Asn | Glu | Arg | Phe | Ile | |
| | | 195 | | | | | 200 | | | | | 205 | | | | |
| ATT | TTG | AGG | TCA | CTT | GTT | CCT | TTT | GTT | ACG | AAA | ATG | GAT | AAA | GCC | TCC | 672 |
| Ile | Leu | Arg | Ser | Leu | Val | Pro | Phe | Val | Thr | Lys | Met | Asp | Lys | Ala | Ser | |
| | 210 | | | | | 215 | | | | | 220 | | | | | |
| ATT | CTT | GGT | GAC | ACC | ATA | GAA | TAT | GTC | AAG | CAG | TTA | CGT | AAG | AAA | GTT | 720 |
| Ile | Leu | Gly | Asp | Thr | Ile | Glu | Tyr | Val | Lys | Gln | Leu | Arg | Lys | Lys | Val | |
| 225 | | | | | 230 | | | | | 235 | | | | | 240 | |
| CAG | GAT | CTT | GAA | GCT | AGA | GCC | AAT | CAG | ACG | GAG | GCT | ACG | CTG | CAG | ACA | 768 |
| Gln | Asp | Leu | Glu | Ala | Arg | Ala | Asn | Gln | Thr | Glu | Ala | Thr | Leu | Gln | Thr | |
| | | | | 245 | | | | | 250 | | | | | 255 | | |
| AAG | GAT | ACA | GGT | ACT | GTG | AAG | GTG | TTG | CAA | GGA | AGG | GGT | AAG | AGG | AGA | 816 |
| Lys | Asp | Thr | Gly | Thr | Val | Lys | Val | Leu | Gln | Gly | Arg | Gly | Lys | Arg | Arg | |
| | | | 260 | | | | | 265 | | | | | 270 | | | |
| ATG | AAG | ATA | GTG | GAA | GGA | AGT | GTT | GGT | GGA | GGA | CAG | GCA | AAG | ATC | ACG | 864 |
| Met | Lys | Ile | Val | Glu | Gly | Ser | Val | Gly | Gly | Gly | Gln | Ala | Lys | Ile | Thr | |
| | | 275 | | | | | 280 | | | | | 285 | | | | |
| GCA | TCT | TCG | CCC | TCA | ACG | ACA | CAT | GAA | GAG | GAG | ATA | GTG | CAA | GTA | GAA | 912 |

| | | | | | | | | | | | | | | |
|---|---|---|---|---|---|---|---|---|---|---|---|---|---|---|
|Ala|Ser|Ser|Pro|Ser|Thr|Thr|His|Glu|Glu|Glu|Ile|Val|Gln|Val|Glu|
| |290| | | |295| | | | |300| | | | | |

| | | | | | | | | | | | | | | | | |
|---|---|---|---|---|---|---|---|---|---|---|---|---|---|---|---|---|
|GTA|TCA|ATT|ATC|GAG|AGT|GAT|GCA|CTG|GTG|GAG|CTC|AGG|TGT|CCA|TAC| 960|
|Val|Ser|Ile|Ile|Glu|Ser|Asp|Ala|Leu|Val|Glu|Leu|Arg|Cys|Pro|Tyr| |
|305| | | | |310| | | | |315| | | | |320| |

| | | | | | | | | | | | | | | | | |
|---|---|---|---|---|---|---|---|---|---|---|---|---|---|---|---|---|
|AAA|GAA|GGG|TTG|TTG|TTA|GAT|GTA|ATC|GAA|ATG|CTA|AGG|GAA|CTT|AAA| 1008|
|Lys|Glu|Gly|Leu|Leu|Leu|Asp|Val|Ile|Glu|Met|Leu|Arg|Glu|Leu|Lys| |
| | | | |325| | | | |330| | | | |335| | |

| | | | | | | | | | | | | | | | | |
|---|---|---|---|---|---|---|---|---|---|---|---|---|---|---|---|---|
|GTG|GAG|GTT|GTA|ACC|ATT|CAA|TCA|TCT|CTT|AAT|AAT|GGC|AGC|TTC|TTT| 1056|
|Val|Glu|Val|Val|Thr|Ile|Gln|Ser|Ser|Leu|Asn|Asn|Gly|Ser|Phe|Phe| |
| | | |340| | | | |345| | | | |350| | | |

| | | | | | | | | | | | | | | | | |
|---|---|---|---|---|---|---|---|---|---|---|---|---|---|---|---|---|
|GCT|GAG|CTG|AGA|GCT|AAG|GTA|AAA|GAG|AAT|ATA|TAT|GGA|AGG|AAA|GCC| 1104|
|Ala|Glu|Leu|Arg|Ala|Lys|Val|Lys|Glu|Asn|Ile|Tyr|Gly|Arg|Lys|Ala| |
| | |355| | | |360| | | | |365| | | | | |

| | | | | | | | | | | | | | | |
|---|---|---|---|---|---|---|---|---|---|---|---|---|---|---|---|
|AAG|CAT|TCT|GGA|AGT|CAA|GAA|GTC|AAT|ACA|CCA|GTT|AAT|CCC| | 1146|
|Lys|His|Ser|Gly|Ser|Gln|Glu|Val|Asn|Thr|Pro|Val|Asn|Pro| | |
|370| | | | |375| | | | |380| | | | | |

TAG      1149

(2) INFORMATION FOR SEQ ID NO:2:

(i) SEQUENCE CHARACTERISTICS:
        (A) LENGTH: 382 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
|Gln|Leu|Asp|Met|Ser|Glu|Ala|Ile|Arg|Phe|Gly|Ser|Pro|Asp|Asp|Gly|
|1| | | |5| | | | |10| | | | |15| |

| | | | | | | | | | | | | | | | |
|---|---|---|---|---|---|---|---|---|---|---|---|---|---|---|---|
|Ser|Asn|Thr|Asn|Met|Asp|Ser|Asp|Phe|His|Met|Val|Gly|Val|Ser|Gln|
| | | |20| | | | |25| | | | |30| | |

| | | | | | | | | | | | | | | | |
|---|---|---|---|---|---|---|---|---|---|---|---|---|---|---|---|
|Ala|Glu|Asn|Pro|Ala|Asp|Tyr|Gln|Arg|Gln|Ala|Glu|Ser|Phe|Lys|Ala|
| | |35| | | | |40| | | | |45| | | |

| | | | | | | | | | | | | | | | |
|---|---|---|---|---|---|---|---|---|---|---|---|---|---|---|---|
|Asp|Thr|Ser|Ile|Ser|Trp|Ala|His|Phe|Gln|Asp|Leu|Pro|His|Leu|Pro|
| |50| | | | |55| | | | |60| | | | |

| | | | | | | | | | | | | | | | |
|---|---|---|---|---|---|---|---|---|---|---|---|---|---|---|---|
|Gly|Gly|Pro|Ser|Tyr|Asp|Glu|Leu|Ser|Gln|Glu|Asp|Thr|His|Tyr|Ser|
|65| | | | |70| | | | |75| | | | |80|

| | | | | | | | | | | | | | | | |
|---|---|---|---|---|---|---|---|---|---|---|---|---|---|---|---|
|Gln|Thr|Val|Ser|Thr|Ile|Leu|Glu|His|Leu|Ser|Asn|Gln|Ser|Ser|Lys|
| | | | |85| | | | |90| | | | |95| |

| | | | | | | | | | | | | | | | |
|---|---|---|---|---|---|---|---|---|---|---|---|---|---|---|---|
|Phe|Ser|Ser|Thr|Ile|Met|Gly|Cys|Ile|Ser|Gln|Thr|Thr|Gln|Ser|Ala|
| | | |100| | | | |105| | | | |110| | |

| | | | | | | | | | | | | | | | |
|---|---|---|---|---|---|---|---|---|---|---|---|---|---|---|---|
|Phe|Thr|Arg|Trp|Pro|Ser|Pro|Ser|Thr|Thr|Val|Ser|Ser|Pro|Phe|Leu|
| | |115| | | | |120| | | | |125| | | |

| | | | | | | | | | | | | | | | |
|---|---|---|---|---|---|---|---|---|---|---|---|---|---|---|---|
|Asp|Gly|Gly|Ala|Thr|Ser|Gly|Gln|Trp|Leu|Leu|Lys|Ser|Ile|Leu|Phe|
| |130| | | | |135| | | | |140| | | | |

| | | | | | | | | | | | | | | | |
|---|---|---|---|---|---|---|---|---|---|---|---|---|---|---|---|
|Ser|Val|Pro|Phe|Leu|His|Thr|Lys|Tyr|Gln|Thr|Ala|Ala|Glu|Val|Ser|
|145| | | | |150| | | | |155| | | | |160|

| | | | | | | | | | | | | | | | |
|---|---|---|---|---|---|---|---|---|---|---|---|---|---|---|---|
|Pro|Lys|Ser|Arg|Asp|Ala|Thr|Thr|Val|Asp|Ser|Ser|Thr|Ala|Ser|Arg|
| | | | |165| | | | |170| | | | |175| |

| | | | | | | | | | | | | | | | |
|---|---|---|---|---|---|---|---|---|---|---|---|---|---|---|---|
|Phe|Arg|Lys|Gly|Cys|Ser|Ile|Thr|Gln|Glu|Glu|Pro|Ser|Gly|Asn|His|
| | | |180| | | | |185| | | | |190| | |

| | | | | | | | | | | | | | | | |
|---|---|---|---|---|---|---|---|---|---|---|---|---|---|---|---|
|Val|Leu|Ala|Glu|Arg|Arg|Arg|Arg|Glu|Lys|Leu|Asn|Glu|Arg|Phe|Ile|
| | |195| | | | |200| | | | |205| | | |

| | | | | | | | | | | | | | | | |
|---|---|---|---|---|---|---|---|---|---|---|---|---|---|---|---|
|Ile|Leu|Arg|Ser|Leu|Val|Pro|Phe|Val|Thr|Lys|Met|Asp|Lys|Ala|Ser|
| |210| | | | |215| | | | |220| | | | |

| | | | | | | | | | | | | | | | |
|---|---|---|---|---|---|---|---|---|---|---|---|---|---|---|---|
|Ile|Leu|Gly|Asp|Thr|Ile|Glu|Tyr|Val|Lys|Gln|Leu|Arg|Lys|Lys|Val|

-continued

| | | | | | | | | | | | | | | | |
|---|---|---|---|---|---|---|---|---|---|---|---|---|---|---|---|
| 225 | | | | | 230 | | | | | 235 | | | | | 240 |
| Gln | Asp | Leu | Glu | Ala | Arg | Ala | Asn | Gln | Thr | Glu | Ala | Thr | Leu | Gln | Thr |
| | | | | 245 | | | | | 250 | | | | | 255 | |
| Lys | Asp | Thr | Gly | Thr | Val | Lys | Val | Leu | Gln | Gly | Arg | Gly | Lys | Arg | Arg |
| | | | 260 | | | | | 265 | | | | | 270 | | |
| Met | Lys | Ile | Val | Glu | Gly | Ser | Val | Gly | Gly | Gly | Gln | Ala | Lys | Ile | Thr |
| | | 275 | | | | | 280 | | | | | 285 | | | |
| Ala | Ser | Ser | Pro | Ser | Thr | Thr | His | Glu | Glu | Glu | Ile | Val | Gln | Val | Glu |
| | 290 | | | | | 295 | | | | | 300 | | | | |
| Val | Ser | Ile | Ile | Glu | Ser | Asp | Ala | Leu | Val | Glu | Leu | Arg | Cys | Pro | Tyr |
| 305 | | | | | 310 | | | | | 315 | | | | | 320 |
| Lys | Glu | Gly | Leu | Leu | Leu | Asp | Val | Ile | Glu | Met | Leu | Arg | Glu | Leu | Lys |
| | | | | 325 | | | | | 330 | | | | | 335 | |
| Val | Glu | Val | Val | Thr | Ile | Gln | Ser | Ser | Leu | Asn | Asn | Gly | Ser | Phe | Phe |
| | | | 340 | | | | | 345 | | | | | 350 | | |
| Ala | Glu | Leu | Arg | Ala | Lys | Val | Lys | Glu | Asn | Ile | Tyr | Gly | Arg | Lys | Ala |
| | | 355 | | | | | 360 | | | | | 365 | | | |
| Lys | His | Ser | Gly | Ser | Gln | Glu | Val | Asn | Thr | Pro | Val | Asn | Pro | | |
| | 370 | | | | | 375 | | | | | 380 | | | | |